US00PP20666P2

(12) United States Plant Patent
Mahon

(10) Patent No.: US PP20,666 P2
(45) Date of Patent: Jan. 19, 2010

(54) SWEET POTATO PLANT NAMED 'MAHON YAM'

(50) Latin Name: *Ipomoea batatas (L.) Lam*
Varietal Denomination: Mahon Yam

(76) Inventor: John A. Mahon, 310 Third St., Cheraw, SC (US) 29520

( * ) Notice: Subject to any disclaimer, the term of this patent is extended or adjusted under 35 U.S.C. 154(b) by 0 days.

(21) Appl. No.: 12/217,597

(22) Filed: Jul. 7, 2008

(51) Int. Cl.
*A01H 5/00* (2006.01)

(52) U.S. Cl. ..... Plt./256

(58) Field of Classification Search ..... Plt./258, Plt./256

See application file for complete search history.

*Primary Examiner*—Annette H Para

(57) ABSTRACT

A new variety of sweetpotato, *Ipomoea batatas*, identified as 'Mahon Yam' is disclosed having superior eating quality. 'Mahon Yam' is characterized by an orange fleshed root that when cooked is sweet, moist and not stringy or fibrous (i.e. creamy). The plant itself is distinguished by unusual leaves for an eating quality sweetpotato, they are seven (7) lobed.

6 Drawing Sheets

SUMMARY OF THE INVENTION

*Ipomoea batatas* 'Mahon Yam' is an orange fleshed, smooth skinned, rose colored, eating quality variety sweetpotato producing yields of superior quality roots that consistently have excellent eating quality due to a combination of sweetness, moistness and creaminess as judged by informal testing. In addition, the leaf is unusual for eating quality sweetpotatoes in that it is normally seven (7) lobed. The 'Mahon Yam' variety has had, when tested, higher sugar content than the USDA standard. The storage roots of 'Mahon Yam' are generally shorter compared to 'Beauregard.'

DESCRIPTION

Latin name of the genus and species: The Latin name of the novel, plant variety disclosed herein is *Ipomoea batatas* (*L.*) Lam.

Variety denomination: The inventive cultivar of *Ipomoea batatas* disclosed herein has been given the varietal denomination 'Mahon Yam.'

BACKGROUND OF THE INVENTION

Sweetpotato (*Ipomoea batatas* ) is a member of the morning glory family Convolvulaceae and unlike Irish potatoes (*Solanum tuberosum*) are not tuber propagated plants. A "tuber" is a short thickened portion of an underground branch derived from an underground stolon and is similar in structure to an aboveground stem. Along a tuber are "eyes" each of which comprises a ridge with a scale-like leaf(like a branch leaf.) This contrasts with sweetpotatoes which produce an edible storage root that is developmentally and anatomically a true root derived from root tissue. Sweetpotatoes do not form tubers.

Historically the dominant sweetpotato variety produced in the United States is 'Beauregard' (unpatented). A new distinct sweetpotato variety named 'Covington' was developed and patented Feb. 26, 2008 and has been grown extensively as a newer variety for sweetpotato commercial food product. The key very significant difference between the plants of the 'Mahon Yam' and 'Beauregard' and 'Covington' plants is that the 'Beauregard' and 'Covington' leaves are cordate to triangular in shape with no slight lobing while the 'Mahon Yam' leaves are deep lobed. Informal tastings have shown the 'Mahon Yam' has excellent flavor, very sweet with excellent mouth feel, and not stringy as compared to many non 'Mahon Yam' commercially available sweetpotatoes.

The color of the flesh of sweetpotatoes varies from cultivar to cultivar; varying from white to orange to purple. Presently the dominant sweetpotatoes which are produced are 'Beauregard' unpatented and 'Covington' patented. This variety 'Mahon Yam' has orange flesh, which is superior for its sweetness, moistness and lack of strings (creamy) as determined by informal reviews by many individuals. This variety is also identified by unusual leaves for an eating quality sweetpotato. The leaves normally have seven (7) distinct lobes.

Lineage: Sweetpotatoes are known to mutate, sport, change readily over time. This is one reason for micropropagation; that is, cultivar stability. It is well known that any variety will run out; conversely, selection of the best mutations may result in a greatly improved sweetpotato. The 'Mahon Yam' variety resulted from continuous, rigorous selection and reselection from over 25 years for eating quality, productivity and visually appealing shape. 'Mahon Yam' originated from a discovery selection of plants grown from storage root derived sprouts from a group of storage roots received from an old farmer in Chesterfield County, S.C. The name of the parent variety is unknown. After some years, the yearly reselection sweetpotatoes were informally compared to the parent variety from the original farm and found to be a darker orange, more attractive, flesh color as well as being sweeter with a smoother mouth feel. The 'Mahon Yam' variety was continued to be cultivated to be improved by further election each and every year until being sent to the NCSU Micropropogation Unit. This particular mutation, the 'Mahon Yam' is excellent for eating with a unique leaf shape for vegetable sweetpotatoes. The best potatoes were sent to the NCSU Micropropagation Unit in order to eliminate viruses and pathogens via mericulture clean up.

Asexual reproduction: 'Mahon Yam' has been asexually propagated via storage roots derived sprouts from continually reselected plants and storage roots since its original selection over twenty-five years ago. Storage and plant selection was done at 310 Third Street, Cheraw, S.C. Each year the most productive, best tasting were selected and the storage roots were separately stored for the next years trials at this location.

The "on farm" trial was conducted at two (2) locations near Cheraw, S.C. from vegetatively, asexually reproduced storage root derived sprouts from stock used for micropropagation. The production was stable, excellent in all respects even during a time of intense drought. Asexual propagation of this new cultivar by cutting and sprouts are stable and the plant produces true to type in successive generations of asexual propagation.

BRIEF DESCRIPTION OF THE DRAWINGS

The photographs in the drawings were made using conventional digital camera photographic techniques and may differ from the colors sited in the detailed botanical description which better accurately describes the new variety.

DETAILED BOTANICAL DESCRIPTION

The following is a detailed description of a new and distinct cultivar of *Ipomoea batatas* plant known by the cultivar name *Ipomoea batatas* 'Mahon Yam.' All colors used in this description refer to The Royal Horticulture Society Colour Chart (The Royal Horticulture Society, London, 1995 Edition), except general terms of ordinary dictionary significance are used where dimensions, sizes, colors, and any other description is given. They are approximations and are used as accurately as practicable. However it is also understood that they may vary with difference in growth, environmental and cultural conditions without any change to the variety 'Mahon Yam.'

Figure 1:
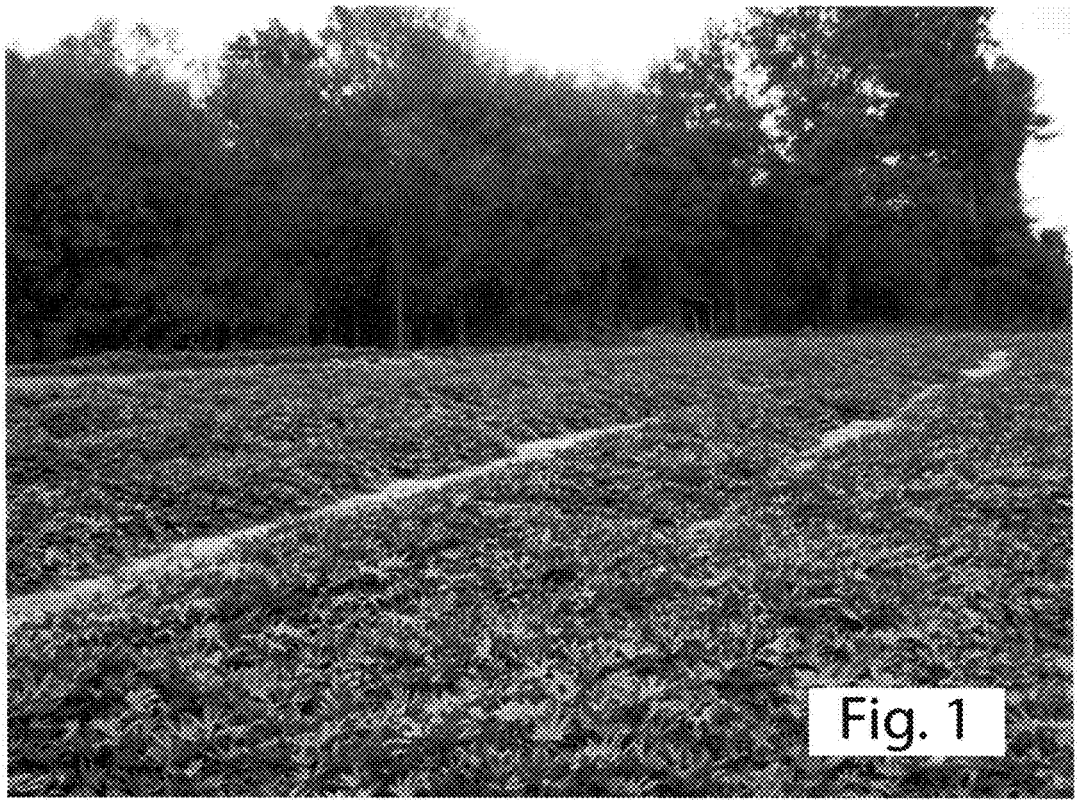
FIG. 1 is a color photograph of the canopy biomass produced by the new variety 'Mahon Yam' in Cheraw, S.C. area. Pictured in FIG. 1, FIG. 2, and FIG. 3 are plants approximately three (3) months after planting on Goldsboro sandy loam two miles north of Cheraw, S.C. on highway U.S. 52 with two separate days of irrigation
Figure 2:
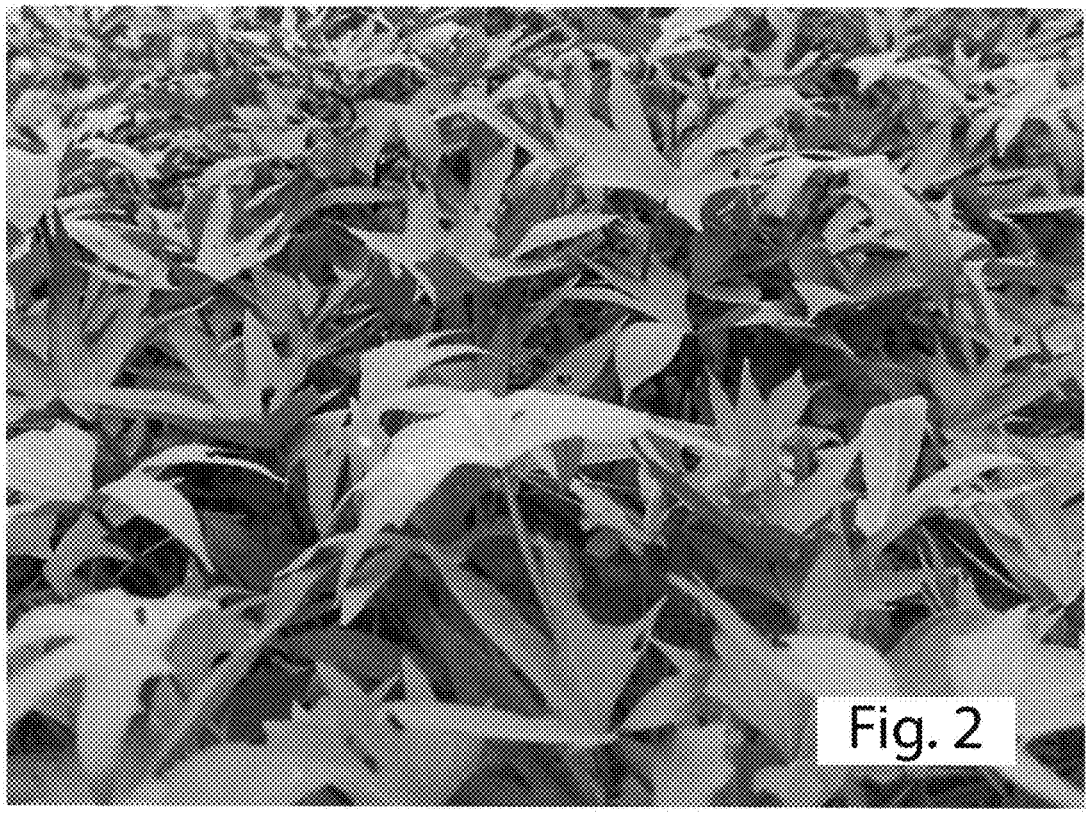
FIG. 2 is a color photograph of the biomass with a clearer view of the leaves in Cheraw, S.C.
Figure 3:
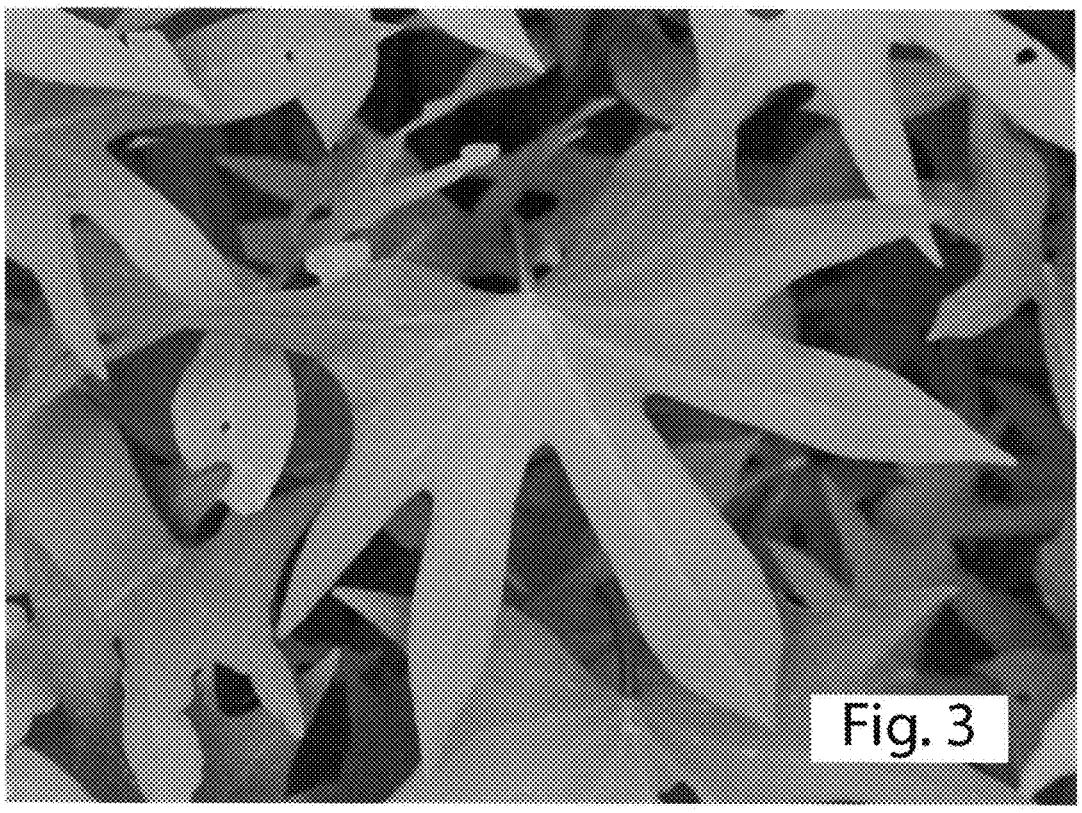
FIG. 3 is a color photograph of the typical leaves of the 'Mahon Yam' variety.

Above ground structural and coloration FIGS. 1, 2 & 3 show the shape and coloration of typical plants *Ipomoea batatas* 'Mahon Yam.' Overall the cultivar is outwardly spreading with a dense canopy. The sweetpotato is greatly affected by soil fertility and water from rain or irrigation. The canopy of the 'Mahon Yam' may spread 6–8' under some conditions.

Figure 4:
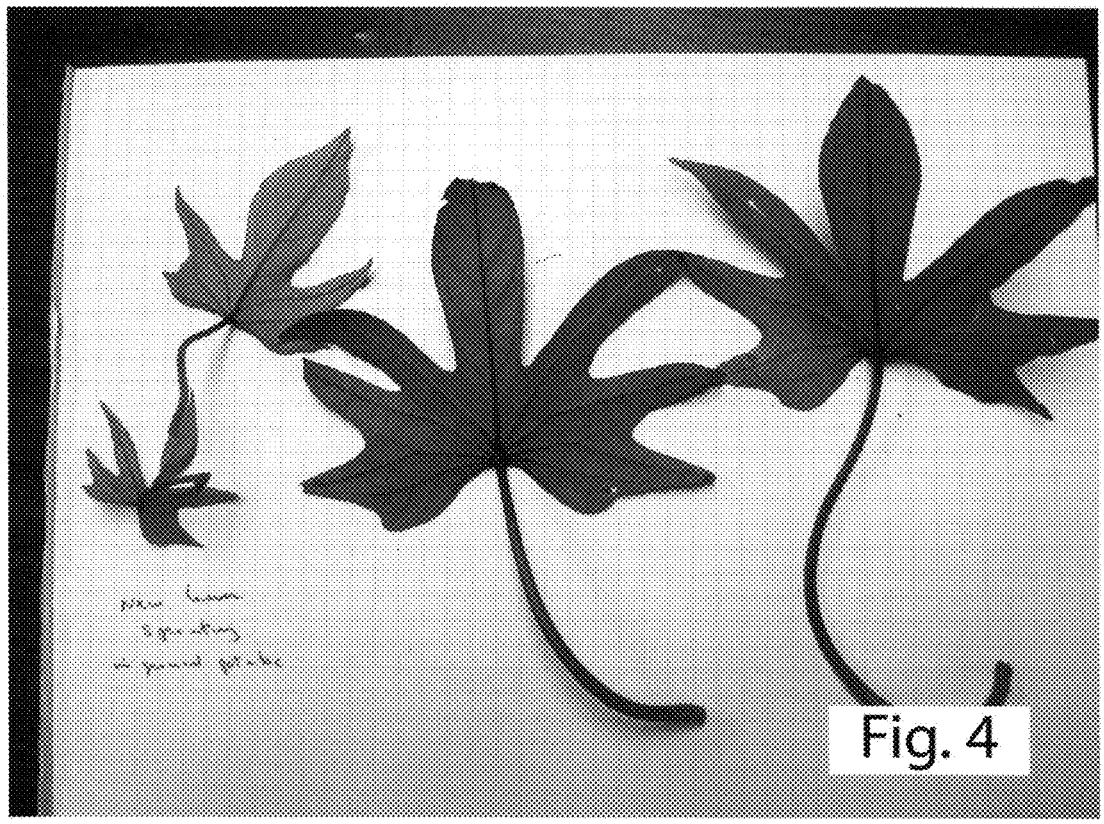
FIG. 4 is a color photograph of typical leaves and petioles of leaves of the 'Mahon Yam' variety with the smaller leaves being newer and not mature. Pictured are leaves from plants five months after planting on Noboco loamy sand at 310 Third Street, Cheraw, S.C. with frequent irrigation.

Foliage: The foliage is striking. Leaves are palmate, lobed and veined alternate and simple in structure. The mature leaves of 'Mahon Yams' normally have seven (7) lobes as shown in FIGS. 3 & 4. A mature leaf may measure 130 mm wide and 100 mm long. Mature leaves measured at 49–50 days after planting (DAP) are difficult to compare in measurement to the leaves of 'Covington' and 'Beauregard' due to the 'Mahon Yam's' deep lobed shape as compared to these others which are cordate to triangular in shape. At 49–50 days the 'Mahon Yam' leaves average 125 mm wide and 103 mm long (tall) as compared to at 45 DAP 'Covington' at 140 mm wide and 135 mm tall, and 'Beauregard' at 112 mm wide and 104 mm tall. The leaf surface area is less in the 'Mahon Yam' than these both. The lobing is a significant difference to other table varieties such as 'Beauregard' and 'Covington.' The lower (back) side of the mature leaf color was 147B with the upper (top) 147A and 147B. The colors of the mature leaves of 'Covington' being top 147A bottom 147B and 'Beauregard' 147A–147B top and 147B bottom are basically similar. Newer leaves and leaves from recently grown sprouts were: 146C lower (back) sides and upper (top) for new leaves; and 146B lower (back) 146A upper (top) for recently grown sprouts. 146 & 147 are in the yellow green group.

Petiole and stem: Petiole, seen in FIG. 4, color was 187A but the color approaches the leaf color on the reverse side of the petiole. Mature leaves petioles measured 9–13 cm and 3–4 mm in diameter. Mature petioles on the 'Mahon Yam' foliage at 49–50 DAP measured somewhat larger than those at 5 months from the planting shown in FIG. 4. The petioles at the base measured 4.4 mm average in diameter and had a petiole average length of 173 mm. They average thinner and shorter than the 'Covington' 6.3 mm and 231 mm and the 'Beauregard' at 5 mm and 187 mm — both at 45 DAP. The stem color is likewise green or green with 187B. 187 is grayed purple group. Note: All data and measurements on 'Covington' and 'Beauregard' are from the U.S. Plant Pat. No. 18,513 P3 dated Feb. 26, 2008 titled Sweetpotato Plant Named 'Covington.'

Figure 5:
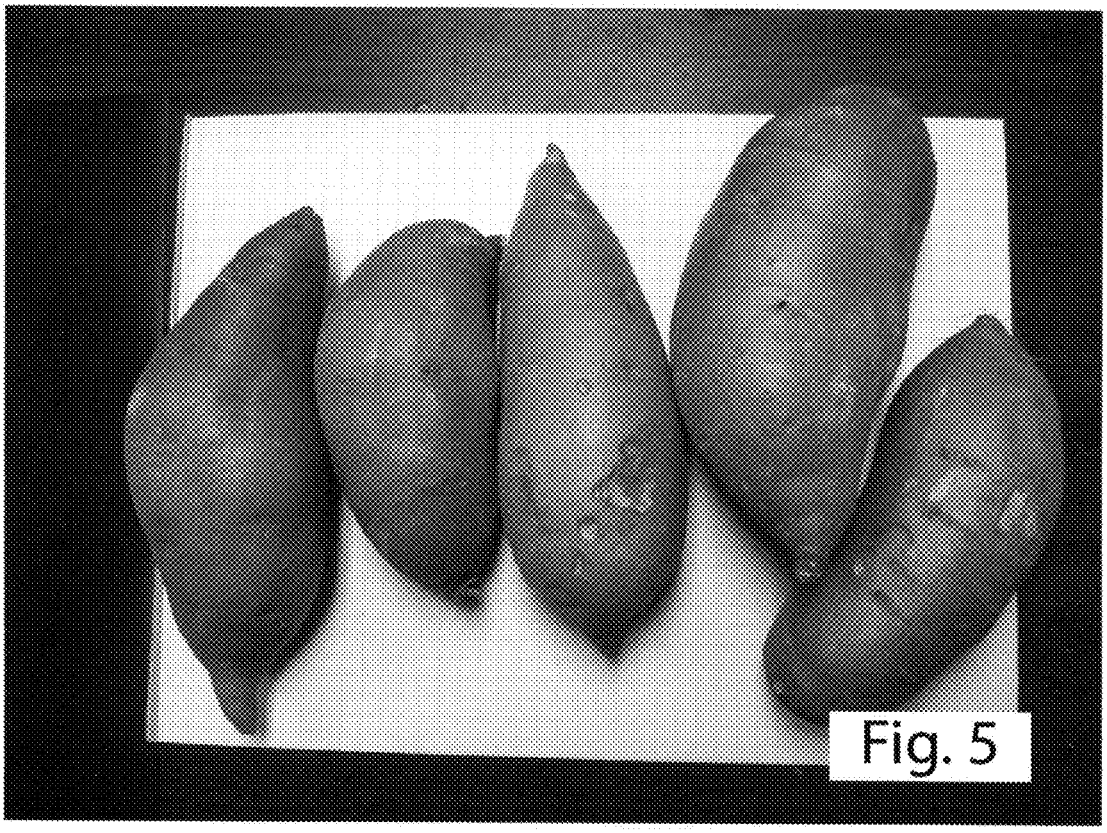
FIG. 5 is a color photograph showing typical roots. Pictured in FIG. 5 and FIG. 6 are roots grown on Goldsboro sandy loam after five months to harvest and two and a half months of storage.
Figure 6:
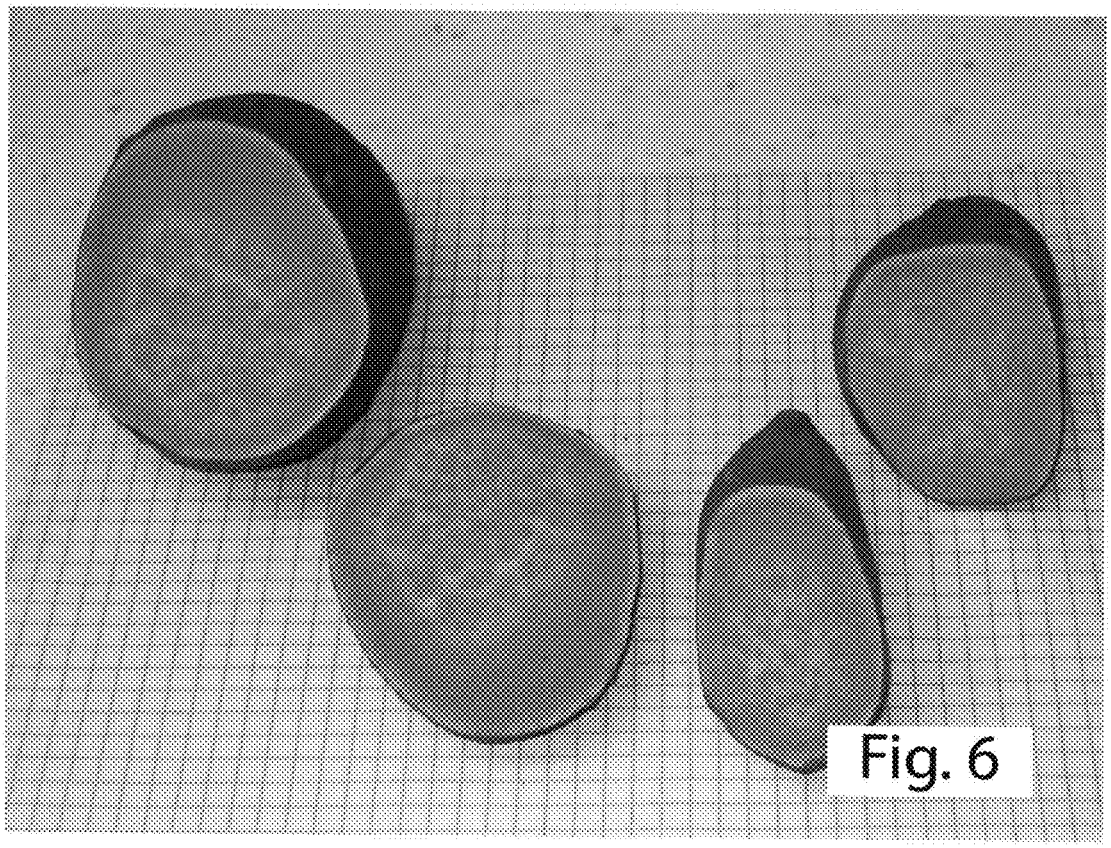
FIG. 6 is a color photograph showing typical root flesh color.

Storage roots: Skin is smooth color generally rose and varies in color; FIG. 5. Colors were 166C, 180B & C, 173, 176B and C and 180 B and C. These colors are in the grayed orange and grayed red group. The flesh, FIG. 6 is orange 28B. A cross section may show areas of 28C and D. 'Covington' produces similarly orange flesh 28B to 28C with 'Beauregard' generally lighter (see note above).

Culinary quality: The flavor of baked storage roots of 'Mahon Yams' has been judged better than other types familiar to the informal tasters. Judged to be sweet, moist and creamy (less stringy). 'Mahon Yam' sweetpotatoes were compared to USDA measurements. Cured 'Mahon Yams' were baked in the skin and tested by Microbac Laboratories, Inc. Southern Testing & Research Division, Wilson, N.C. and averaged 11.81 grams/100 grams total sugars with starch at 8.84 grams/100 grams while the USDA measurements of baked in skin sweet potatoes (edible portion) were 6.48 grams/100 grams total sugars with 7.05 grams/100 grams starch.. This is significant.

The invention claimed is:

1. A new distinct cultivar of *Ipomoea batatas* plant named 'Mahon Yam' substantially as illustrated and described herein.

* * * * *